US011944479B2

(12) United States Patent
Ono

(10) Patent No.: US 11,944,479 B2
(45) Date of Patent: Apr. 2, 2024

(54) MEDICAL IMAGE DIAGNOSIS APPARATUS, X-RAY COMPUTED TOMOGRAPHY APPARATUS, AND MEDICAL IMAGE DIAGNOSIS ASSISTING METHOD

(71) Applicant: CANON MEDICAL SYSTEMS CORPORATION, Otawara (JP)

(72) Inventor: Nobuhide Ono, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 325 days.

(21) Appl. No.: 17/062,659

(22) Filed: Oct. 5, 2020

(65) Prior Publication Data

US 2021/0113175 A1    Apr. 22, 2021

(30) Foreign Application Priority Data

Oct. 16, 2019   (JP) .................................. 2019-189614

(51) Int. Cl.
*A61B 6/00*    (2006.01)
*A61B 6/08*    (2006.01)
(Continued)

(52) U.S. Cl.
CPC ................ *A61B 6/488* (2013.01); *A61B 6/08* (2013.01); *A61B 6/4447* (2013.01); *A61B 6/461* (2013.01);
(Continued)

(58) Field of Classification Search
CPC ......... A61B 6/488; A61B 6/08; A61B 6/4447; A61B 6/461; A61B 6/467; A61B 6/58; A61B 6/032; A61B 6/0407; A61B 6/0492; A61B 5/055; A61B 5/706; G01R 33/283; G01R 33/543
See application file for complete search history.

(56) References Cited

U.S. PATENT DOCUMENTS 4,259,725 A * 3/1981 Andrews .................. G09G 5/08
    348/E5.056
6,490,477 B1 * 12/2002 Zylka ...................... A61B 6/583
    600/417

(Continued)

FOREIGN PATENT DOCUMENTS

JP    S 64-022871    1/1989
JP    09313475 A * 12/1997 ............. A61B 6/548
(Continued)

OTHER PUBLICATIONS

Japanese Office Action dated Jun. 20, 2023, issued in Japanese Patent Application No. 2019-227212.

*Primary Examiner* — Sean D Mattson
(74) *Attorney, Agent, or Firm* — Oblon, McClelland, Maier & Neustadt, L.L.P.

(57) ABSTRACT

A medical image diagnosis apparatus according to an embodiment includes a gantry and a processor. The gantry includes an imaging system configured to perform an imaging process on a subject by using one of radiation and magnetism. The processor is configured to generate a second image by combining a first image acquired by imaging the subject while using an optical imaging device different from the imaging system, with a plane related to an imaging position in the imaging process using the imaging system.

20 Claims, 8 Drawing Sheets

(51) Int. Cl.
  *A61B 6/46* (2024.01)
  *A61B 6/58* (2024.01)
  *A61B 6/03* (2006.01)
  *A61B 6/04* (2006.01)
(52) U.S. Cl.
  CPC ............. *A61B 6/467* (2013.01); *A61B 6/58* (2013.01); *A61B 6/032* (2013.01); *A61B 6/0407* (2013.01); *A61B 6/0492* (2013.01)

(56) References Cited

U.S. PATENT DOCUMENTS

| | | | | |
|---|---|---|---|---|
| 11,357,462 B2* | 6/2022 | Huang | ................. | G06T 7/0012 |
| 2008/0024127 A1* | 1/2008 | Nagao | ............... | G01R 33/56375 |
| | | | | 324/301 |
| 2009/0021257 A1* | 1/2009 | Yasuhara | ............. | G01R 33/283 |
| | | | | 324/318 |
| 2012/0093384 A1* | 4/2012 | Goto | ................... | G01R 33/543 |
| | | | | 382/131 |
| 2012/0243655 A1* | 9/2012 | Ninomiya | ............ | A61B 6/4035 |
| | | | | 378/8 |
| 2015/0164440 A1* | 6/2015 | Rackow | ............... | A61B 5/7485 |
| | | | | 600/427 |
| 2016/0074004 A1* | 3/2016 | Braun | .................... | G06F 3/017 |
| | | | | 378/205 |
| 2016/0174930 A1* | 6/2016 | Braun | .................. | A61B 6/4417 |
| | | | | 378/205 |
| 2017/0049529 A1* | 2/2017 | Hannemann | ......... | G01R 33/543 |
| 2018/0140270 A1* | 5/2018 | Profio | .................. | A61B 6/0407 |
| 2018/0235559 A1* | 8/2018 | Mc Carthy | .......... | A61B 6/4085 |
| 2019/0069871 A1 | 3/2019 | Tkaczyk et al. | | |
| 2020/0085385 A1 | 3/2020 | Nye et al. | | |

FOREIGN PATENT DOCUMENTS

| | | | |
|---|---|---|---|
| JP | 2011-029557 A | | 2/2011 |
| JP | 2017063839 A | * | 4/2017 |
| JP | 2019-080909 A | | 5/2019 |

* cited by examiner

FIG.6
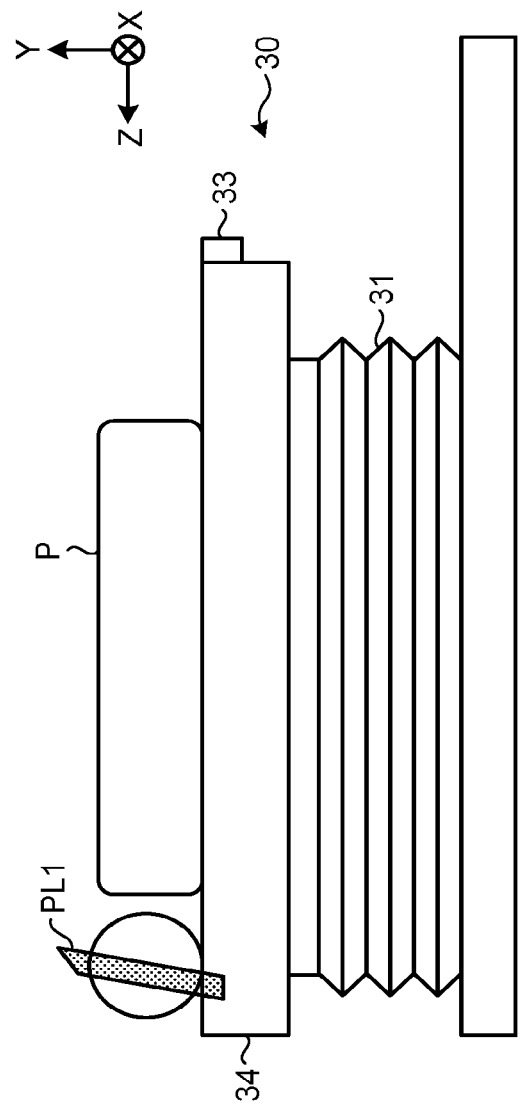
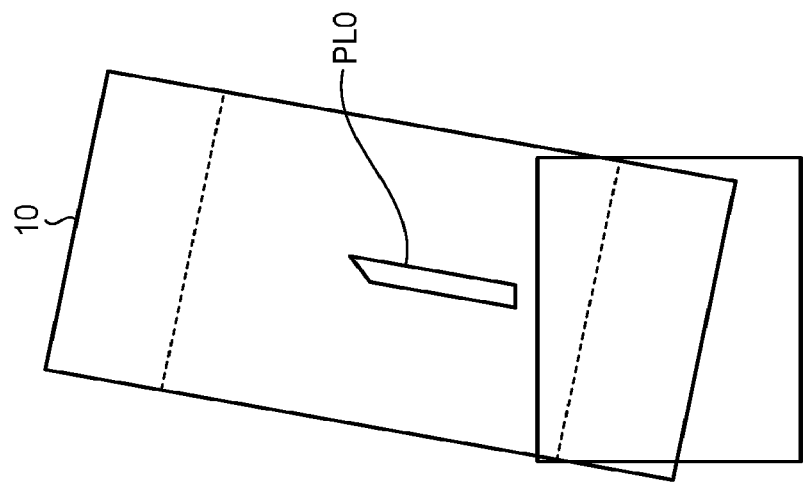

MEDICAL IMAGE DIAGNOSIS APPARATUS, X-RAY COMPUTED TOMOGRAPHY APPARATUS, AND MEDICAL IMAGE DIAGNOSIS ASSISTING METHOD

CROSS-REFERENCE TO RELATED APPLICATION(S)

This application is based upon and claims the benefit of priority from Japanese Patent Application No. 2019-189614, filed on Oct. 16, 2019; the entire contents of which are incorporated herein by reference.

FIELD

Embodiments described herein relate generally to a medical image diagnosis apparatus, an X-ray computed tomography apparatus, and a medical image diagnosis assisting method.

BACKGROUND

With X-ray Computed Tomography (CT) apparatuses, to check an imaged cross-section position or an imaged range (which hereinafter may be referred to as "an imaged cross-section position or the like"), a lighting instrument (an area lighting instrument) configured to project laser light onto a couchtop may be used in some situations. The area lighting instrument is, for example, able to project a position or a region corresponding to an imaged cross-section position or the like of a main imaging process, onto the couchtop. By visually recognizing the position or the range indicated by the light projected from the area lighting instrument onto the couchtop, a user is able to check the imaged cross-section position or the like of the main X-ray imaging process, while preventing the subject from being exposed to radiation.

However, to check the imaged cross-section position or the like by using the area lighting instrument, the user needs, before the imaging process, to go from a manipulation room to an examination room, so as to perform a position aligning process next to the patient. Further, the display of the imaged cross-section position or the like presented by the area light projector indicates only the surface on which the laser is projected. For this reason, it would not be possible to see a line in the depth direction where radiation exposure occurs while the gantry is tilted. It would therefore be difficult to accurately understand whether an area that needs to be protected is avoided without fail.

BRIEF DESCRIPTION OF THE DRAWINGS

FIG. 6 is a drawing illustrating an example of a combined image obtained on the basis of an image from the optical imaging device C2, similarly while the gantry is tilted;

DETAILED DESCRIPTION

Figure 1:
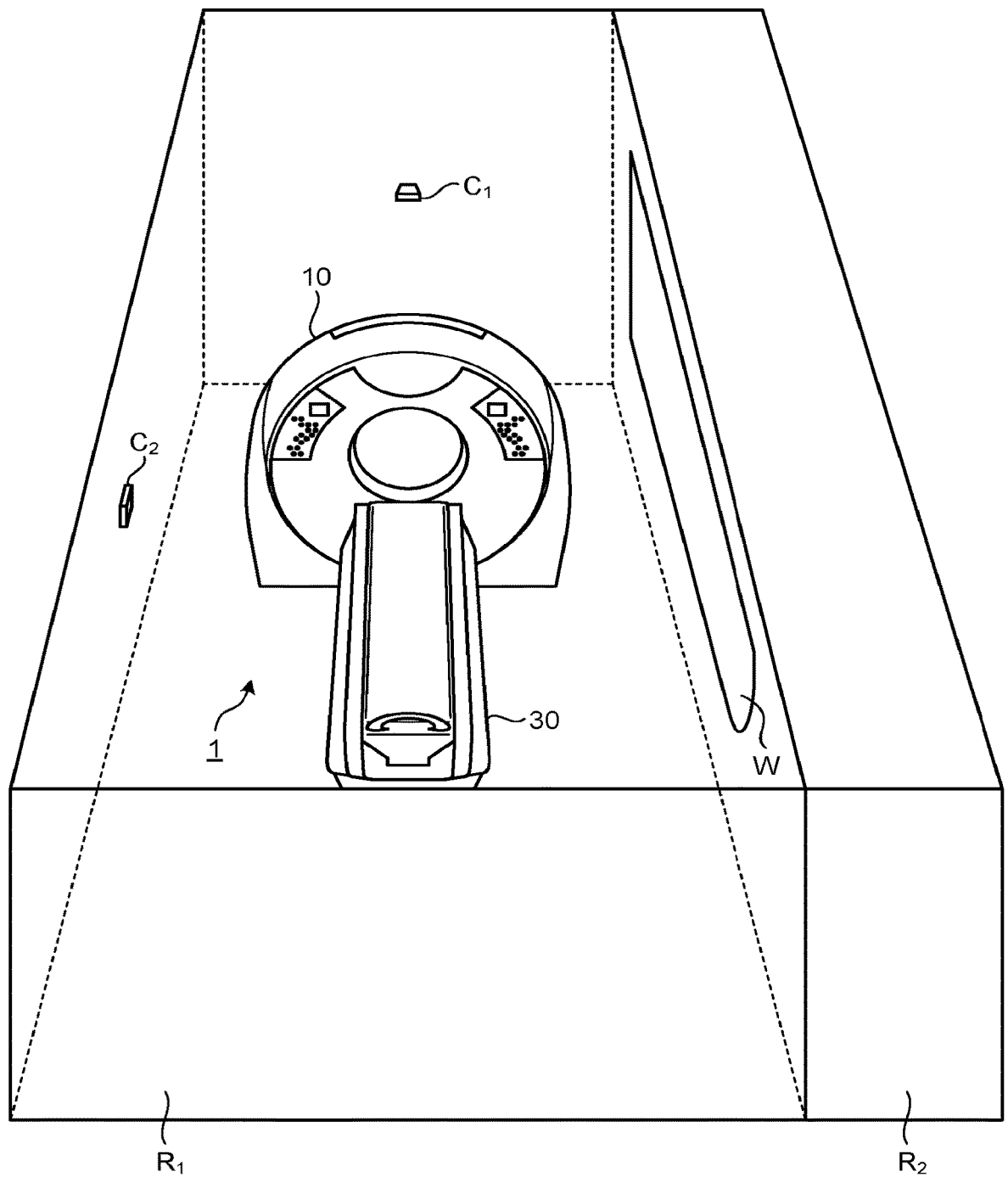
FIG. 1 is a drawing illustrating an example of an environment in which an X-ray CT apparatus 1 is installed.

A medical image diagnosis apparatus according to an embodiment includes a gantry and a processor. The gantry includes an imaging system configured to perform an imaging process on a subject by using one of radiation and magnetism. The processor is configured to generate a second image by combining a first image acquired by imaging the subject while using an optical imaging device different from the imaging system, with a plane related to an imaging position in the imaging process using the imaging system.

The following will describe a first embodiment and a second embodiment with reference to the accompanying drawings. In the explanations below, some of the constituent elements having substantially the same functions and configurations will be referred to by using the same reference characters, and duplicate explanations will be provided only when necessary. Further, it is possible to combine each of the embodiments with another embodiment or certain conventional techniques, as long as no conflict occurs in the configurations.

First Embodiment

To begin with, an environment in which an X-ray CT apparatus 1 according to a first embodiment is installed will be explained. FIG. 1 is a drawing illustrating an example of the environment in which the X-ray CT apparatus 1 is installed.

As illustrated in FIG. 1, the X-ray CT apparatus 1 includes a gantry 10, a couch 30, and a console (not illustrated in FIG. 1). The gantry 10 and the couch 30 are installed in an examination room R1. The console is installed in a manipulation room R2 provided next to the examination room R1. A user is able to view the status of the examination room R1 through a window W of the manipulation room R2 and is able to go back and forth between the examination room R1 and the manipulation room R2 through a door (not illustrated). The gantry 10 and the couch 30 operate on the basis of operations from the user via the console or operations from the user via an operation unit provided for the gantry 10 or for the couch 30.

On the ceiling of the examination room R1, an optical imaging device C1 represented by a digital camera, an infrared ray camera, or the like is provided. Further, on a wall of the examination room R1, an optical imaging device C2 similarly realized with a digital camera, an infrared ray camera, or the like is provided.

The optical imaging device C1 is configured to image the gantry 10 and the couch 30 from the top faces thereof. The optical imaging device C2 is configured to image the gantry 10 and the couch 30 from lateral faces thereof. The optical imaging device C2 may be configured to image either of the left and right lateral faces of the gantry 10 and the couch 30.

The imaging processes by the optical imaging devices C1 and C2 are continuously performed, for example, after a subject (hereinafter, "patient") is placed on a couchtop 33 of the couch 30 until an imaged cross-section position is determined. The images taken by the optical imaging devices C1 and C2 are sequentially forwarded to the X-ray CT apparatus 1 in a real-time manner.

Figure 2:
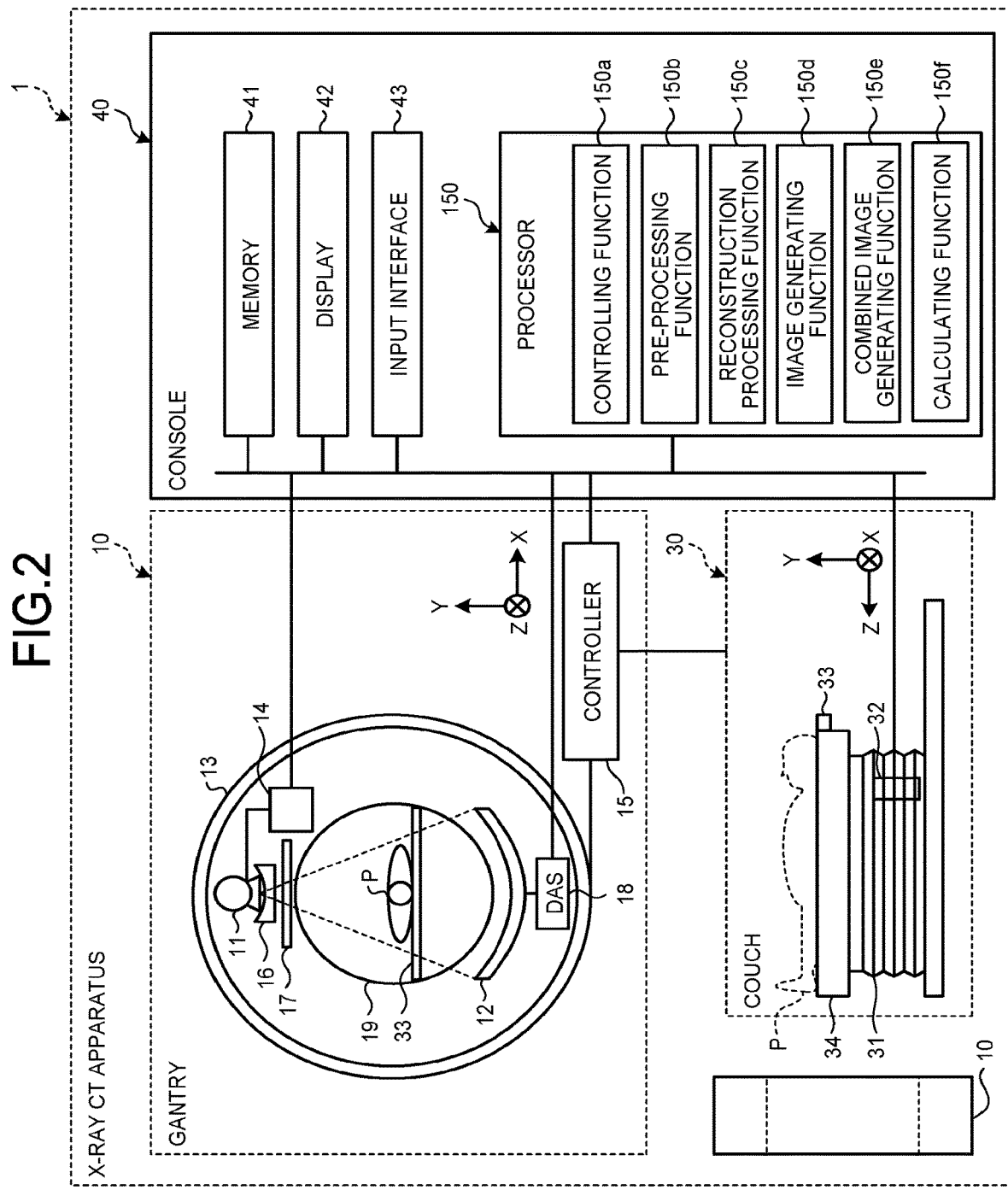
FIG. 2 is a block diagram illustrating an exemplary configuration of an X-ray CT apparatus according to a first embodiment.

Next, an outline of a configuration of the X-ray CT apparatus 1 will be explained. FIG. 2 is a block diagram illustrating an exemplary configuration of the X-ray CT apparatus 1 according to the first embodiment. As illustrated in FIG. 2, the X-ray CT apparatus 1 according to the embodiment includes the gantry 10, the couch 30, and a console 40.

In the present embodiment, the rotation axis of a rotating frame 13 in a non-tilted state and the longitudinal direction of the couchtop 33 of the couch 30 is defined as a Z-axis direction; the axial direction orthogonal to the Z-axis direction and parallel to the floor surface is defined as an X-axis direction; and the axial direction orthogonal to the Z-axis direction and perpendicular to the floor surface is defined as a Y-axis direction.

The gantry 10 includes an imaging system used for taking medical images used in diagnosis processes. In other words, the gantry 10 is a device including the imaging system configured to radiate X-rays onto a patient P and to acquire projection data from detection data of X-rays that have passed through the patient P. The gantry 10 includes an X-ray tube 11, a wedge 16, a collimator 17, an X-ray detector 12, an X-ray high-voltage device 14, a Data Acquisition System (DAS) 18, the rotating frame 13, a controller 15, and the couch 30.

The X-ray tube 11 is a vacuum tube in which thermo electrons are emitted from a negative pole (a filament) toward a positive pole (a target), by application of high voltage from the X-ray high-voltage device 14.

The wedge 16 is a filter used for adjusting the X-ray dose of the X-rays radiated from the X-ray tube 11. More specifically, the wedge 16 is a filter configured to pass and attenuate the X-rays radiated from the X-ray tube 11, so that the X-rays radiated from the X-ray tube 11 onto the patient P have a predetermined distribution.

For example, the wedge 16 may be a wedge filter or a bow-tie filter and is a filter obtained by processing aluminum so as to have a predetermined target angle and a predetermined thickness.

The collimator 17 is configured with lead plates or the like used for narrowing down the radiation range of the X-rays that have passed through the wedge 16 and is configured to form a slit with a combination of the plurality of lead plates or the like.

The X-ray detector 12 is configured to detect the X-rays that were radiated from the X-ray tube 11 and have passed through the patient P and to output an electrical signal corresponding to the amount of X-rays to the data acquisition system (the DAS 18). The X-ray detector 12 includes, for example, a plurality of rows of X-ray detecting elements in each of which a plurality of X-ray detecting elements are arranged in a channel direction along an arc centered on a focal point of the X-ray tube 11. The X-ray detector 12 includes, for example, a plurality of rows of X-ray detecting elements in each of which a plurality of X-ray detecting elements are arranged in a channel direction along an arc centered on a focal point of the X-ray tube. For example, the X-ray detector 12 has a structure in which the plurality of rows of X-ray detecting elements in each of which the plurality of X-ray detecting elements are arranged in the channel direction are arranged in a slice direction (which may be referred to as a body-axis direction or a row direction).

Further, for example, the X-ray detector 12 is a detector of an indirect conversion type including a grid, a scintillator array, and an optical sensor array. The scintillator array includes a plurality of scintillators. Each of the scintillators includes a scintillator crystal that outputs light having a photon quantity corresponding to the amount of the X-rays that have become incident thereto. The grid is disposed on the surface of the scintillator array positioned on the X-ray incident side and includes an X-ray blocking plate having a function of absorbing scattered X-rays. The optical sensor array has a function of converting outputs from the scintillators into electric signals corresponding to the amounts of light and may include, for example, optical sensors such as photomultiplier tubes (PMTs). Alternatively, the X-ray detector 12 may be a detector of a direct conversion type including a semiconductor element configured to convert the incident X-rays into electrical signals.

The X-ray high-voltage device 14 includes: a high-voltage generating device including electric circuits such as a transformer, a rectifier, and the like and having a function of generating the high voltage to be applied to the X-ray tube 11; and an X-ray controller configured to control the output voltage in accordance with the X-rays radiated by the X-ray tube 11. The high-voltage generating device may be of a transformer type or of an inverter type. Further, the X-ray high-voltage device 14 may be provided for the rotating frame 13 or may be provided on the side of a fixed frame (not illustrated) of the gantry 10. In this situation, the fixed frame is a frame configured to rotatably support the rotating frame 13.

The DAS 18 includes an amplifier configured to perform an amplifying process on the electrical signals output from the X-ray detecting elements of the X-ray detector 12 and an Analog/Digital (A/D) converter configured to convert the electrical signals into digital signals. The DAS 18 is configured to generate the detection data. The detection data generated by the DAS 18 is transferred to the console 40.

The rotating frame 13 is an annular frame configured to support the X-ray tube 11 and the X-ray detector 12 so as to oppose each other and configured to rotate the X-ray tube 11 and the X-ray detector 12 via the controller 15. In addition to supporting the X-ray tube 11 and the X-ray detector 12, the rotating frame 13 may also further support the X-ray high-voltage device 14 and the DAS 18. In an example, the detection data generated by the DAS 18 is transmitted by optical communication, from a transmitter provided on the rotating frame 13 and including a light emitting diode, to a receiver provided in a non-rotation part (e.g., the fixed frame) of the gantry 10 and including a photodiode, so as to be transferred to the console 40. The method for transmitting the detection data from the rotating frame 13 to the non-rotation part of the gantry 10 is not limited to optical communication and may be realized with any of other contactless data transfer methods.

The controller 15 includes: a processor having a Central Processing Unit (CPU) or the like; and a driving mechanism configured with a motor, an actuator, and/or the like. The controller 15 has a function of receiving an input signal from an input interface 43 attached to the console 40 or an input interface attached to the gantry 10 and controlling operations of the gantry 10 and the couch 30. Further, the controller 15 is configured to exercise control, upon receipt of input signals, to cause the rotating frame 13 to rotate and to cause the gantry 10 and the couch 30 to operate.

For example, on the basis of tilting angle (tilt angle) information input by the input interface attached to the gantry 10 or tilting angle information based on a virtual plane received from a controlling function 150a, the controller 15 is configured to tilt the gantry 10 by causing the rotating frame 13 to rotate on an axis extending parallel to the X-axis direction. The controller 15 and the controlling function 150a included in a processor 150 are each an example of a controlling unit.

In this situation, the virtual plane is a plane set in a predetermined position on the couchtop 33 and is used as a reference at the times when, during an imaging process, the moving of a base 31 and the couchtop 33 of the couch 30 is controlled and when the tilting of the gantry 10 is controlled. In other words, at the time of the imaging process, the controller 15 is configured to control the base 31 and the couchtop 33 of the couch 30 and the gantry 10 so that the virtual plane coincides with an imaging plane. In this situation, the imaging plane is a plane corresponding to a cross-section image acquired from the imaging process and may be, for example, a plane having the Z-axis as a normal line thereof and being positioned at the center of the X-ray detector 12 in terms of the Z-axis direction.

The couch 30 is a device on which the patient P to be scanned is placed and which is configured to move the patient P. The couch 30 includes the base 31, a couch driving device 32, the couchtop 33, and a supporting frame 34. The base 31 is a casing that supports the supporting frame 34 so as to be movable in the vertical directions. The couch driving device 32 is a motor or an actuator configured to move the couchtop 33 on which the patient P is placed, along the long axis directions thereof (i.e., the Z-axis direction in FIG. 1). The couchtop 33 provided on the top face of the supporting frame 34 is a board on which the patient P is placed. In this situation, in addition to the couchtop 33, the couch driving device 32 may move the supporting frame 34 along the long axis directions of the couchtop 33.

The couch driving device 32 is configured to move the base 31 in up-and-down directions according to control signals from the controller 15. The couch driving device 32 is configured to move the couchtop 33 along the long axis directions, according to control signals from the controller 15. In other words, the couch driving device 32 is configured to control at least one of the base 31 and the couchtop 33 so that the virtual plane coincides with an actual imaged cross-section.

The console 40 is a device configured to receive operations performed by the user on the X-ray CT apparatus 1 and to reconstruct X-ray CT image data from the X-ray detection data acquired by the gantry 10. The console 40 includes a memory 41, a display 42, the input interface 43, and the processor 150.

For example, the memory 41 is realized by using a semiconductor memory element such as a Random Access Memory (RAM) or a flash memory, or a hard disk, an optical disk, or the like. The memory 41 is configured to store therein the projection data and reconstructed image data, for example. The memory 41 is an example of a storage unit.

The display 42 is a monitor referenced by the user and is configured to display various types of information. For example, the display 42 is configured to output a medical image (a CT image) generated by the processor 150, a Graphical User Interface (GUI) used for receiving various types of operations from the user, and the like. For example, the display 42 may be a liquid crystal display or a Cathode Ray Tube (CRT) display. The display 42 is an example of the display circuit.

The input interface 43 is configured to receive the various types of input operations from the user, to convert the received input operations into electrical signals, and to output the electrical signals to the processor 150. For example, the input interface 43 is configured to receive, from the user, an acquisition condition used at the time of acquiring the projection data, a reconstruction condition used at the time of reconstructing the CT image, an image processing condition used at the time of generating a post-processing image from the CT image, and the like. For example, the input interface 43 is realized by using a mouse, a keyboard, a trackball, a switch, a button, a joystick, and/or the like. The input interface 43 is an example of an input unit.

The processor 150 is configured to control operations of the entirety of the X-ray CT apparatus 1. For example, the processor 150 includes the controlling function 150a, a pre-processing function 150b, a reconstruction processing function 150c, an image generating function 150d, a combined image generating function 150e, and a calculating function 150f. In an embodiment, processing functions performed by the constituent elements, namely, the controlling function 150a, the pre-processing function 150b, the reconstruction processing function 150c, the image generating function 150d, the combined image generating function 150e, and the calculating function 150f, are stored in the memory 41 in the form of computer-executable programs. The processor 150 is a processor configured to realize the functions corresponding to the programs, by reading and executing the programs from the memory 41. In other words, the processor 150 that has read the programs has the functions illustrated within the processor 150 in FIG. 1.

With reference to FIG. 1, the example was explained in which the single processor (i.e., the processor 150) realizes the processing functions performed by the controlling function 150a, the pre-processing function 150b, the reconstruction processing function 150c, the image generating function 150d, the combined image generating function 150e, and the calculating function 150f. It is, however, also acceptable to structure the processor 150 by combining together a plurality of independent processors, so that the functions are realized as a result of the processors executing the programs.

In other words, each of the abovementioned functions may be configured as a program, so that the single processor executes the programs. Alternatively, one or more specific functions may be implemented in a dedicated independent program executing circuit.

The term "processor" used in the above explanations denotes, for example, a Central Processing Unit (CPU), a Graphical Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 41. Instead of saving the programs in the memory 41, it is also acceptable to directly incorporate the programs in the circuits of the one or more processors. In that situation, the one or more processors realize the functions by reading and executing the programs incorporated in the circuits thereof.

By employing the controlling function 150a, the processor 150 is configured to control the various types of functions of the processor 150, on the basis of input operations received from the user via the input interface 43. By employing the pre-processing function 150b, the processor 150 is configured to generate data obtained by performing a pre-processing process such as a logarithmic converting process, an offset process, an inter-channel sensitivity correcting process, a beam hardening correction, or the like, on the detection data output from the DAS 18. The data before the pre-processing process (the detection data) and the data after the pre-processing process may collectively be referred to as projection data. By employing the reconstruction processing function 150c, the processor 150 is configured to generate CT image data by performing a reconstructing process using a filtered back-projection method, a successive approximation reconstruction method, or the like, on the projection data generated by the pre-processing function 150b. By employing the image generating function 150d, the processor 150 is configured to convert the CT image data generated by the reconstruction processing function 150c into tomographic image data on an arbitrary cross-section or into three-dimensional image data, by using a publicly-known method, on the basis of an input operation received from the user via the input interface 43.

Further, by employing the combined image generating function 150e, the processor 150 is configured to generate a combined image serving as a second image, by combining a first image acquired by imaging the gantry 10 and the couch 30 while using the optical imaging devices C1 and C2, with a plane related to the imaging position in the imaging process using the imaging system of the gantry 10. In other words, by employing the combined image generating function 150e, the processor 150 is configured to generate the combined image in which a virtual plane (e.g., a rectangular plate-like plane) is set on the couchtop 33 of the couch 30 by using an Augmented Reality (AR) technique, for example, on the basis of the images received from the optical imaging devices C1 and C2.

Further, by employing the combined image generating function 150e, the processor 150 is configured to generate a combined image in which a median line is set on the couchtop 33 of the couch 30, on the basis of the images received from the optical imaging devices C1 and C2.

In this situation, the median line is a straight line parallel to the longitudinal direction of the couchtop 33 and is typically a centerline with respect to the width direction (the X-axis direction) of the couchtop 33. In this situation, similarly to the imaging position, to indicate the median line, a combined image in which a virtual plane is set on the couchtop 33 may be generated.

Figure 3:
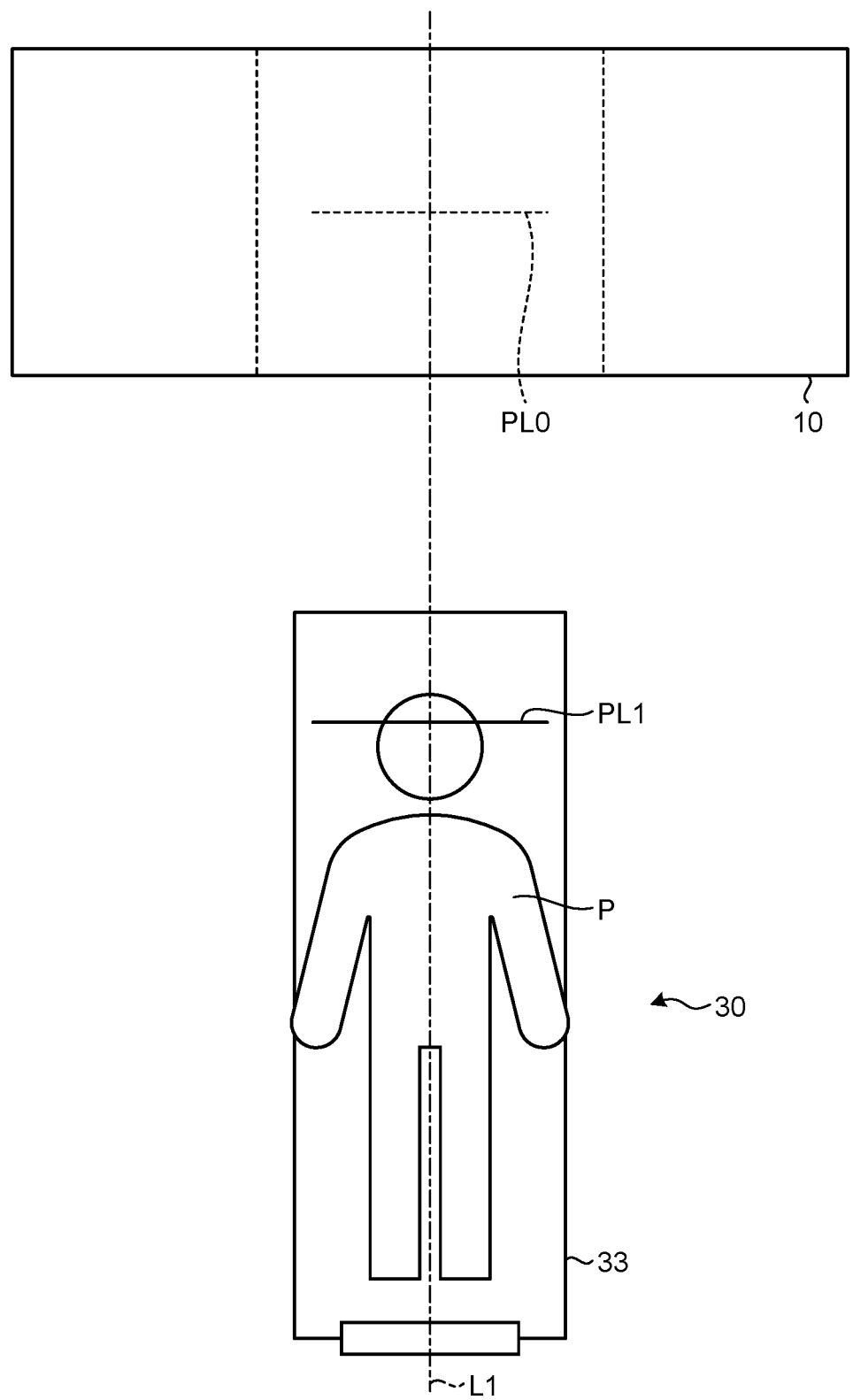
FIG. 3 is a drawing illustrating an example of a combined image obtained by combining an image acquired by an optical imaging device C1 with a virtual plane.
Figure 4:
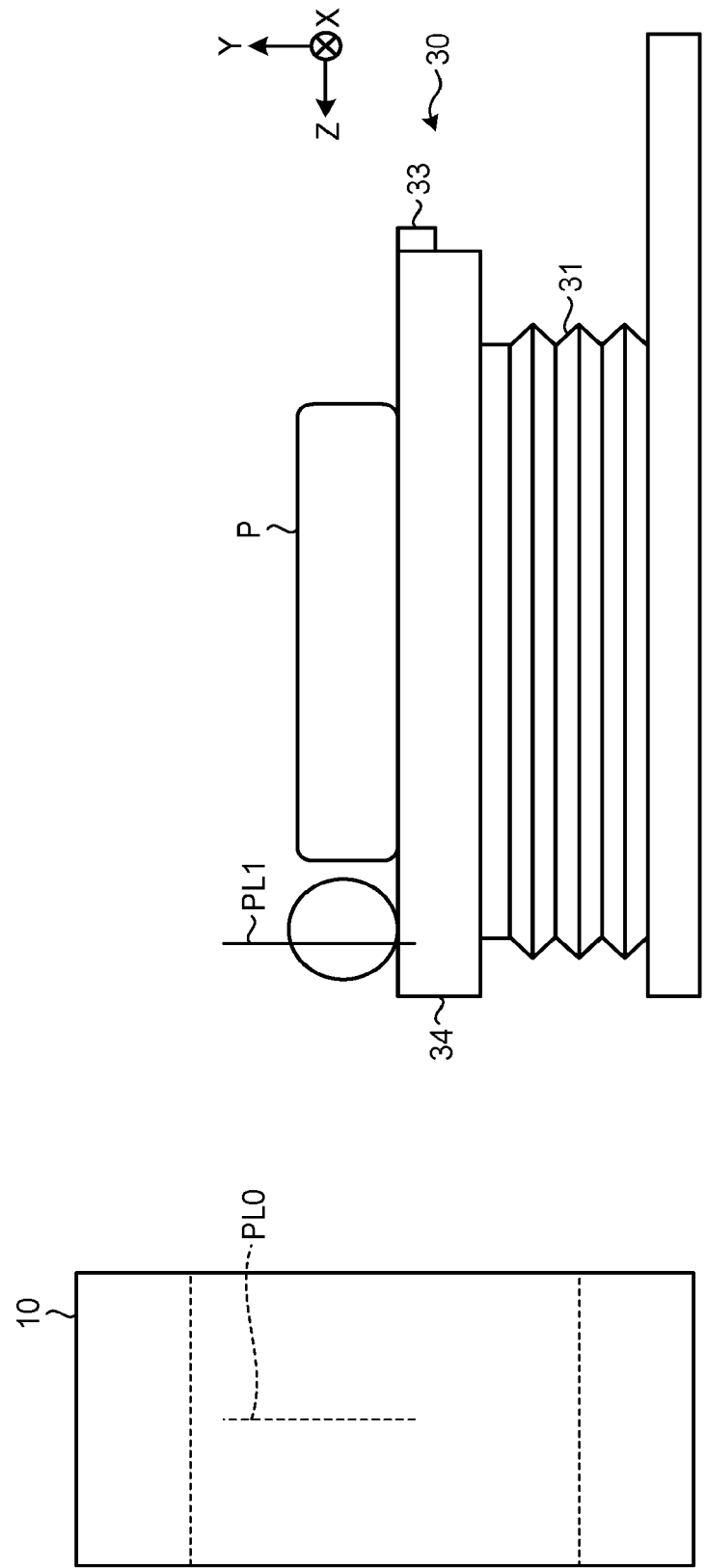
FIG. 4 is a drawing illustrating an example of a combined image obtained by combining an image acquired by an optical imaging device C2 with the virtual plane.

FIG. 3 is a drawing illustrating an example of a combined image obtained by combining an image acquired by the optical imaging device C1 with a virtual plane PL1. Further, FIG. 4 is a drawing illustrating an example of a combined image obtained by combining an image acquired by the optical imaging device C2 with the virtual plane PL1. The plane PL0 in FIGS. 3 and 4 simulatively indicates the imaging plane.

As illustrated in FIGS. 3 and 4, in the combined images generated by the combined image generating function 150e, the virtual plane PL1 and the median line L1 are displayed on the couchtop 33.

Figure 5:
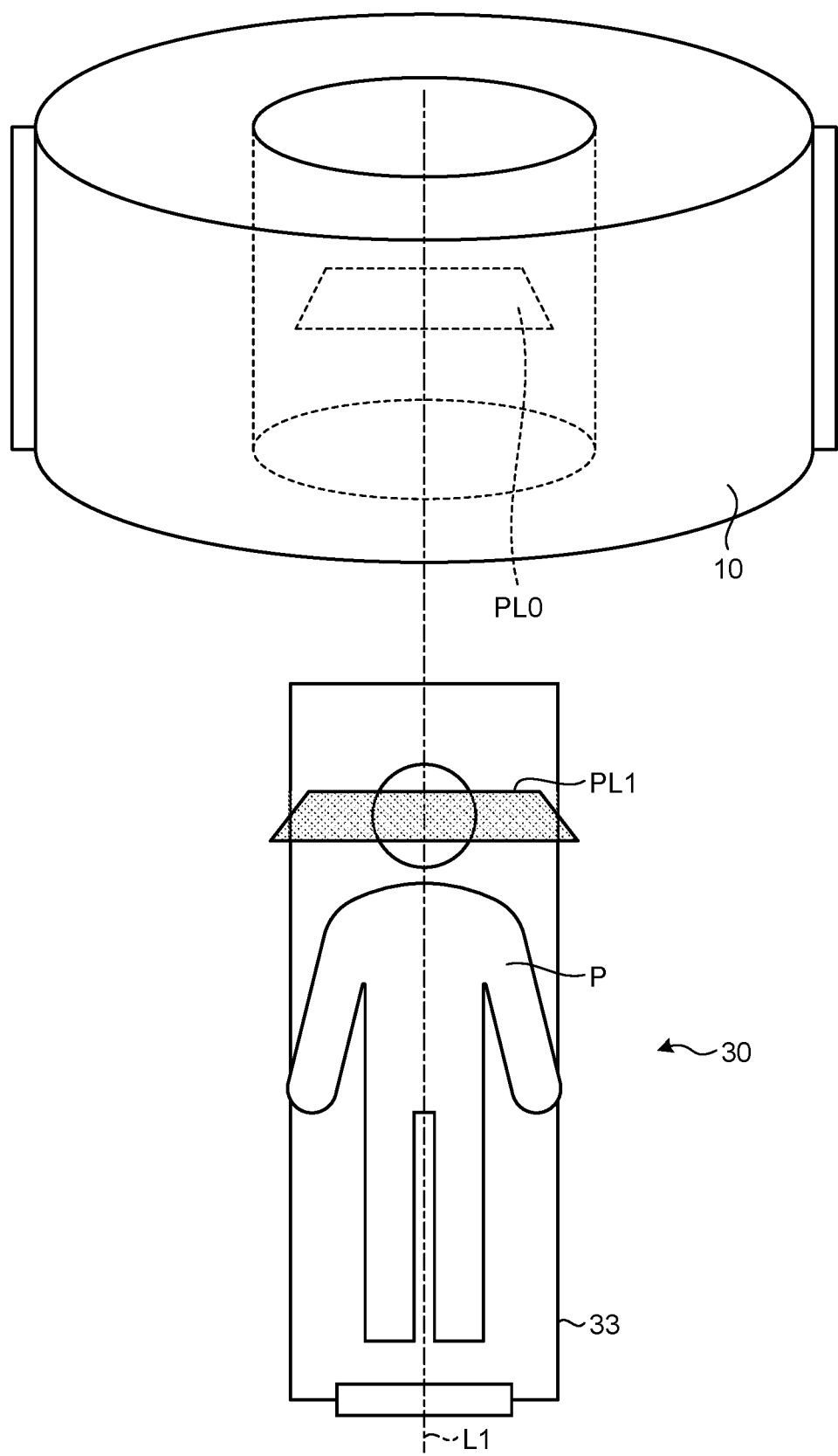
FIG. 5 is a drawing illustrating an example of a combined image obtained on the basis of an image from the optical imaging device C1, while a gantry is tilted.

Further, FIG. 5 is a drawing illustrating an example of a combined image obtained on the basis of an image from the optical imaging device C1, while the gantry 10 is tilted. Similarly, FIG. 6 is a drawing illustrating an example of a combined image obtained on the basis of an image from the optical imaging device C2, while the gantry 10 is tilted.

As illustrated in FIGS. 5 and 6, while the gantry 10 is tilted, the virtual plane PL1 is also displayed as being tilted in conjunction with the gantry 10. The user is able to view, in the manipulation room R2, the combined images illustrated in FIGS. 3 to 6 that are displayed on the display 42, for example. On the display 42, the user can adjust the position of the virtual plane PL1 with respect to the patient P so that the virtual plane PL1 coincides with the imaging plane PL0 indicating the cross-section of the patient P to be imaged. The position adjusting process may be performed by using a mouse, for example, or may be performed as a fingertip operation when the display 42 displaying the combined images is a touch panel.

To facilitate the explanations, FIGS. 3 to 6 illustrate the examples of the combined images rendering the gantry 10. The user, however, aligns the position of the imaged cross-section, by adjusting, within a combined image, the position of the virtual plane PL1 with respect to the patient P. Accordingly, the combined images do not necessarily have to display the gantry 10.

Returning to the description of FIG. 2, by employing the calculating function 150f, the processor 150 is configured to calculate a display position of the virtual plane. In other words, by employing the calculating function 150f, the processor 150 is configured to calculate a relative positional relationship between the gantry 10 and the couchtop 33 at present (e.g., a relative positional relationship between a reference position of the gantry 10 and a reference position of the couchtop 33), on the basis of the images received from the optical imaging devices C1 and C2. By employing the calculating function 150f, the processor 150 is configured to further calculate a position in which the virtual plane PL1 is displayed on the couchtop 33 at present, on the basis of the calculated relative positional relationship between the gantry 10 and the couchtop 33.

Further, when the relative positional relationship between the gantry 10 and the couchtop 33 has been changed, the same process is performed on the basis of images taken by the optical imaging devices C1 and C2 of the gantry 10 and the couchtop 33 after the change.

Further, by employing the calculating function 150f, the processor 150 is configured to calculate information about the tilting angle of the gantry 10, a moving amount of the couchtop 33 in the up-and-down direction, and a moving amount of the couchtop 33 in the longitudinal direction, on the basis of the position and the angle of the virtual plane at present. In other words, by employing the calculating function 150f, the processor 150 calculates the information about the tilting angle of the gantry 10, the moving amount of the couchtop 33 in the up-and-down direction, and the moving amount of the couchtop 33 in the longitudinal direction that will cause the virtual plane at present to coincide with the imaging plane.

Next, a flow in a process performed by the X-ray CT apparatus according to the present embodiment, from an imaged cross-section position setting process using the virtual plane, to the start of an imaging process will be explained.

Figure 7:
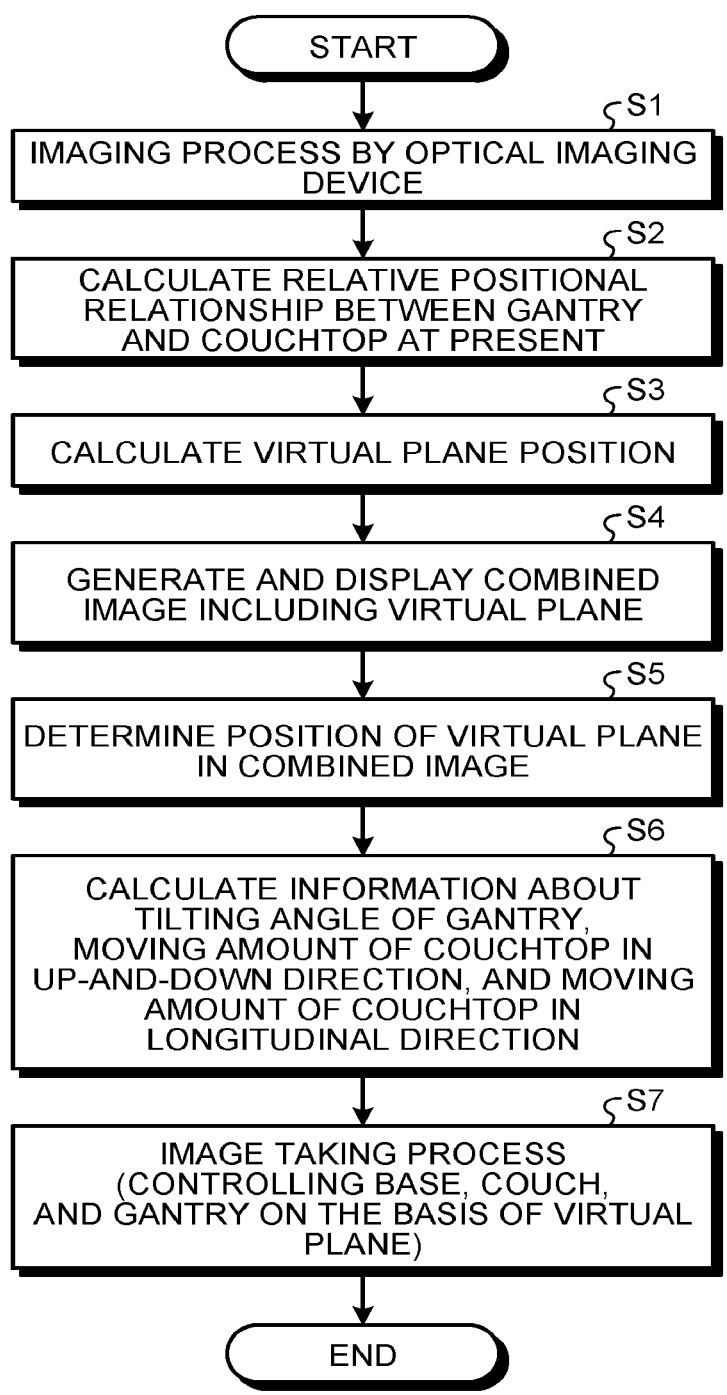
FIG. 7 is flowchart illustrating an example of a flow in a process performed by the X-ray CT apparatus, from an imaged cross-section position setting process to the start of an imaging process.

FIG. 7 is flowchart illustrating an example of the flow in the process performed by the X-ray CT apparatus, from the imaged cross-section position setting process to the start of the imaging process.

First, before the patient P is set at step S1, patient information is registered into an examination appointment list, and details are input. After that, as illustrated in FIG. 7, the imaging process by the optical imaging devices C1 and C2 is started (step S1).

In this situation, the imaging process is started at step S1 typically while the patient P is placed on the couchtop 33. Alternatively, however, the imaging process may be started at step S1 before the patient P is placed on the couchtop 33.

For example, the imaging process performed by the optical imaging devices C1 and C2 is continuously performed after the patient is placed on the couchtop 33 of the couch 30 until an imaged cross-section position is determined. The images taken by the optical imaging devices C1 and C2 are sequentially forwarded to the X-ray CT apparatus 1 in a real-time manner.

Subsequently, by employing the calculating function 150f, the processor 150 calculates a relative positional relationship between the gantry 10 and the couchtop 33 at present, on the basis of the images received from the optical imaging devices C1 and C2 (step S2). On the basis of the calculated relative positional relationship between the gantry 10 and the couchtop 33, the processor 150 calculates a position in which the virtual plane PL1 is displayed on the couchtop 33 at present (step S3).

After that, by employing the combined image generating function 150e, the processor 150 generates a combined image by combining the images received from the optical imaging devices C1 and C2 with a plate-like figure indicating the virtual plane and a straight line indicating the median line and causes the display 42 to display the generated combined image (step S4).

Subsequently, the position of the virtual plane is determined in the combined image (step S5). For example, according to a user input through the input interface 43, an instruction is input to adjust the position and the angle of the virtual plane displayed on the display 42. By employing the combined image generating function 150e, the processor 150 changes the position and the angle of the virtual plane in the combined image.

In this situation, by enlarging or shrinking the combined image on the display 42, it is possible to fine-tune the position and the angle of the virtual plane. For example, when a cross-section of the head is imaged, the user adjusts, while viewing the combined images illustrated in FIGS. 3 to 6, the position of the virtual plane PL1 on a screen of the display unit, so that the virtual plane PL1 is arranged in a desired position of the head of the patient P. For example, the user adjusts the position and the tilting angle of the virtual plane, while visually recognizing a line of radiation exposure on the monitor, so as to avoid tissues that are highly sensitive to radiation such as the eyeballs (the crystalline lenses) of the patient P.

After that, by employing the calculating function 150f, the processor 150 calculates information about a tilting angle of the gantry 10, a moving amount of the couchtop 33 in the up-and-down direction, and a moving amount of the couchtop 33 in the longitudinal direction that will cause the virtual plane to coincide with the imaging plane (step S6).

Subsequently, the controller 15 performs an imaging process by controlling the gantry 10 and the couch 30 so that the virtual plane coincides with the imaging plane (step S7).

The X-ray CT apparatus 1 according to the present embodiment described above includes: the gantry 10 including the imaging system; the couch 30 including the couchtop 33; and the combined image generating function 150e serving as an image generating unit configured to generate the second image by combining the first image acquired by imaging the gantry 10 and the couch 30 while using the optical imaging devices C1 and C2, with the virtual plane serving as a plane related to the imaging position in the imaging process using the imaging system of the gantry 10.

In the actual imaging process, the gantry 10 and the couch 30 are controlled so that, for example, the virtual image coincides with the imaged cross-section. Accordingly, by adjusting the position and the angle of the virtual plane displayed on the monitor, the user is able to set the imaged cross-section with respect to the patient easily and accurately. As a result, it is possible to shorten the operation time period required by the imaged cross-section position aligning process.

The virtual plane is displayed on the display unit while reflecting not only the positions in the X-, Y-, and Z-directions, but also the tilting angle of the gantry 10. Accordingly, the user is able to adjust the position and the tilting angle of the virtual plane while visually recognizing the line of radiation exposure on the display 42, so as to avoid tissues that are highly sensitive to radiation such as the eyeballs (the crystalline lenses). As a result, by checking the imaged cross-section including the tilt line with the use of AR, it is possible, without fail, to prevent the sites that need to be protected from being exposed to the radiation.

Further, the monitor is configured to display the images obtained by combining the patient images taken by the cameras, with the plate-like figure indicating the cross-section position and the straight line indicating the median line. It is therefore possible to determine the imaging position by moving the couch and the gantry tilt with conventional remote operations using the console, while viewing the monitor. Accordingly, it is possible to set and adjust the virtual plane in the manipulation room. As a result, the user is able to perform the series of imaging processes while staying in the manipulation room, without the need to travel between the examination room and the manipulation room.

First Modification Example

The X-ray CT apparatus 1 according to the first embodiment is configured to generate and display the combined image including the virtual plane corresponding to the imaging plane and the median line. Alternatively, it is also possible to generate and display a combined image further including information corresponding to an imaged range.

On the basis of the set imaged range and the relative positional relationship between the gantry 10 and the couchtop 33, the processor 150 is configured, by employing the calculating function 150f, to calculate the position, in terms of the body-axis direction, of a boundary plane PL2 of the imaged range closer to the gantry 10 and the position, in terms of the body-axis direction, of a boundary plane PL3 of the imaged range farther from the gantry 10. By employing the combined image generating function 150e, the processor 150 generates a combined image obtained by combining the images received from the optical imaging devices C1 and C2, with the virtual plane PL1, the boundary planes PL2 and PL3 indicating the boundaries of the imaged range, and the median line L1.

In this situation, it is also possible to display the planes in mutually-different colors, to make it possible to distinguish the virtual plane PL1 and the boundary planes PL2 and PL3 indicating the boundaries of the imaged range from one another.

By using the X-ray CT apparatus 1 according to the first modification example, it is possible to set, easily and accurately, the imaged range in addition to the imaged cross-section. As a result, it is possible to shorten the operation time period required by the aligning processes for the imaged cross-section and the imaged range.

Second Modification Example

In the above example, the X-ray CT apparatus 1 according to the first embodiment is configured to display, on the display 42 in the manipulation room R2, the combined image including the virtual plane corresponding to the imaging plane and the median line. Alternatively, it is also possible to display the combined image including the virtual plane corresponding to the imaging plane and the median line on a tablet Personal Computer (PC). With this arrangement, it is possible to perform the position aligning process anywhere, without being limited to the manipulation room and the examination room.

Third Modification Example

The function of determining the position of the imaged cross-section that uses the virtual plane explained in the above embodiment is naturally applicable to standing CT apparatuses. In that situation, for example, one of the optical imaging devices C1 and C2 is arranged on the wall to the front of the patient, whereas the other of the two optical imaging devices C1 and C2 is arranged on a fall facing a lateral side of the patient.

Fourth Modification Example

The applicable range of the function of determining the position of the imaged cross-section that uses the virtual plane explained in the above embodiment is not limited to X-ray CT apparatuses. It is possible to apply the function to a medical image diagnosis apparatus including a gantry having an imaging system and a couch, such as a magnetic resonance imaging apparatus, a Positron Emission Tomography (PET) apparatus, or a Single Photon Emission Computed Tomography (SPECT) apparatus.

Fifth Modification Example

In the first embodiment, the virtual plane is displayed as a rectangle. Naturally, the rectangle is merely an example of the virtual plane. It is possible to use any figure that symbolically represents the virtual plane corresponding to the imaging plane, such as a square plane, a perfectly circular plane, or an oval plane. One of the shape and the size of the figure may correspond to one of the following: one of the shape and the size of the opening formed in the gantry; and one of the shape and the size of a Field Of View (FOV) with which the imaging process is performed by the gantry.

Sixth Modification Example

Some X-ray CT apparatuses do not include a gantry tilting mechanism. In those situations, it is also acceptable to generate and display a combined image including a virtual plane, by using only the images from the optical imaging device C1, as necessary.

Second Embodiment

Next, an X-ray CT apparatus according to a second embodiment will be explained. The X-ray CT apparatus according to the second embodiment is applied to a multi-room solution system in which a gantry is shared by a plurality of systems, by moving the gantry between a plurality of examination rooms.

In the following sections, an example will be explained in which the present disclosure is applied to an angio-CT system serving as a two-room system in which the gantry is moved between two examination rooms; however, the number of examination rooms is not limited to that in the present example.

Figure 8:
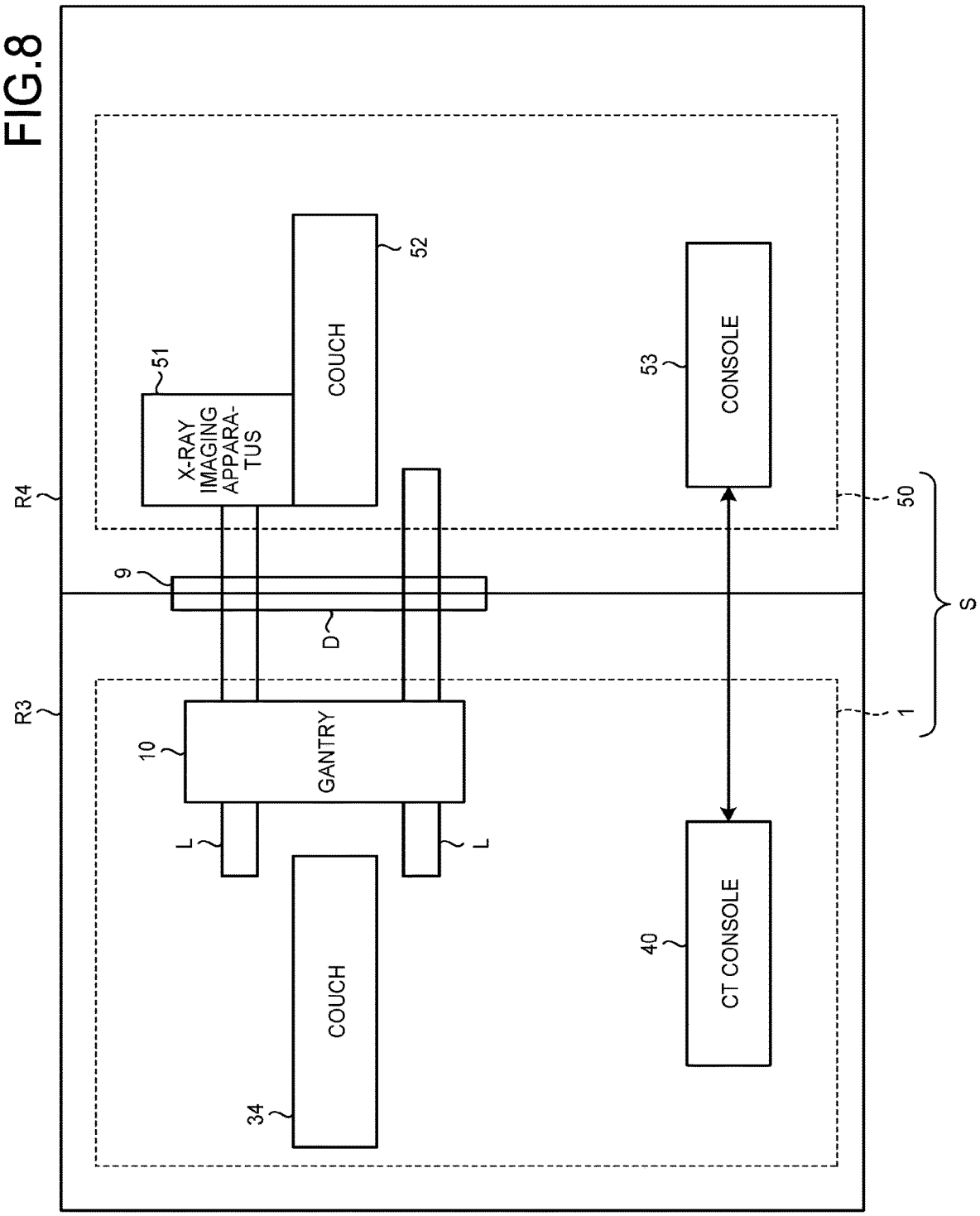
FIG. 8 is a diagram illustrating an exemplary configuration of an angio-CT system S in which a gantry 10 is shared between two modalities.

FIG. 8 is a diagram illustrating an exemplary configuration of an angio-CT system S in which the gantry 10 is shared between two modalities.

As illustrated in FIG. 8, the angio-CT system S includes the X-ray CT apparatus 1 and an X-ray imaging system 50 represented by an angiography ("Angio") apparatus. In the examination room R3, the X-ray CT apparatus 1 is provided. Further, in the examination room R4 positioned adjacent to the examination room R3, the X-ray imaging system 50 is provided. It is possible to partition the examination room R3 and the examination room R4 by using an open/close door D.

The X-ray imaging system 50 includes an X-ray imaging apparatus 51 serving as an imaging system, a couch 52, and a console 53. The X-ray imaging system 50 and the X-ray CT apparatus 1 are able to communicate with each other via Controller Area Network (CAN) communication or the like, for example.

The gantry 10 of the X-ray CT apparatus 1 is provided so as to be movable between the plurality of examination rooms R3 and R4 by using a transport rail L, for example. In the angio-CT system S, the gantry 10 configured to implement X-ray computed tomography on patients is shared between modalities provided in the examination rooms R3 and R4. In other words, in the angio-CT system, the gantry 10 is shared between the examination rooms R3 and R4 (i.e., between the couches 4 and 7).

Although not illustrated, the optical imaging device C1 is installed in such a position on the ceiling of the examination room R3 that makes it possible to simultaneously image both the installation position of the gantry 10 (the reference position of the gantry 10) and the couch 30 of the X-ray CT apparatus 1, during an X-ray CT imaging process. Further, the optical imaging device C2 is installed in such a position on a wall facing a lateral side of the gantry 10 in the examination room R3 that makes it possible to simultaneously image both the installation position of the gantry 10 and the couch 34 of the X-ray CT apparatus 1, during the X-ray CT imaging process.

In the angio-CT system S structured in this manner, the processor 150 of the X-ray CT apparatus 1 is configured to calculate, by employing the calculating function 150f, a relative positional relationship between the installation position of the gantry 10 and the couchtop 33 at present during the X-ray CT imaging process, on the basis of images received from the optical imaging devices C1 and C2. By employing the calculating function 150f, the processor 150 is configured to calculate a position in which the virtual plane PL1 is displayed on the couchtop 33 at present, on the basis of the calculated relative positional relationship. By using the obtained results, it is possible, similarly to the first embodiment, to realize the process of aligning the position of the imaged cross-section and the like by using the virtual plane PL1.

By using the X-ray CT apparatus 1, even when the gantry 10 is in the examination room R4, and not in the examination room R3, it is possible to adjust the imaged cross-section position by using the virtual plane, prior to the X-ray computed tomography process, while the patient is placed on the couchtop 33 of the couch 30 and waiting for his/her turn to be imaged. Accordingly, it is possible to improve the rate of operation of the multi-room solution system compared to that in conventional examples.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis apparatus comprising:
   a gantry including an imaging system configured to perform an imaging process on a subject by using one of radiation and magnetism;
   a couch having a couchtop on which the subject is placed; and
   a processor configured to
      generate a first image acquired by imaging the gantry and the couchtop of the couch on which the subject is placed while using an optical imaging device different from the imaging system,
      calculate, on a basis of a relative positional relationship between the gantry and the couchtop in the first image, at least one of position or angle of an imaging plane in the first image, the imaging plane being a plane related to an imaging position used in the imaging process by the imaging system, and
      generate a second image by combining the first image with the imaging plane on a basis of the calculated at least one of position or angle.

2. The medical image diagnosis apparatus according to claim 1, wherein the processor generates the second image by using, as the imaging plane, a figure having one selected from among rectangular, square, oval, and circular shapes to indicate the imaging position.

3. The medical image diagnosis apparatus according to claim 2, wherein one of the shape and a size of the figure correspond to one of the following: one of a shape and a size of an opening formed in the gantry; and one of a shape and a size of a field of view with which the imaging process is performed by the gantry.

4. The medical image diagnosis apparatus according to claim 1, wherein the processor generates the second image by combining together: one of a line and a plane corresponding to a median line of the subject, the first image, and the imaging plane.

5. The medical image diagnosis apparatus according to claim 1, wherein the processor generates the imaging plane corresponding to a tilting angle of the gantry.

6. The medical image diagnosis apparatus according to claim 1, further comprising: an input interface circuit configured to change, in the second image displayed by a display circuit, one or both of the position and the angle of the imaging plane related to the imaging position, in response to an input from a user, wherein
   on a basis of the imaging plane that has been changed, the processor controls at least one of: the gantry; and the couch.

7. The medical image diagnosis apparatus according to claim 6, being provided with a portable terminal including the display circuit and the input interface circuit.

8. The medical image diagnosis apparatus according to claim 1, wherein the first image renders one of the gantry and a reference position of the gantry.

9. The medical image diagnosis apparatus according to claim 1, wherein the processor is configured to generate the second image by combining the first image with the imaging plane, a virtual plane, a boundary plane indicating boundaries of an imaging range, and a median line.

10. The medical image diagnosis apparatus according to claim 1, wherein the processor is configured to generate the second image by setting the imaging plane within the imaging system.

11. The medical image diagnosis apparatus according to claim 1, wherein the processor is configured to:
   generate the second image by setting the imaging plane within the imaging system and setting a virtual plane on the first image.

12. An X-ray computed tomography apparatus comprising:
   a gantry including an imaging system configured to perform an imaging process on a subject by using radiation;
   a couch having a couchtop on which the subject is placed; and
   a processor configured to
      generate a first image acquired by imaging the gantry and the couchtop of the couch on which the subject is placed while using an optical imaging device different from the imaging system,
      calculate, on a basis of a relative positional relationship between the gantry and the couchtop in the first image, at least one of position or angle of an imaging plane in the first image, the imaging plane being a plane related to an imaging position used in the imaging process by the imaging system, and
      generate a second image by combining the first image with the imaging plane on a basis of the calculated at least one of position or angle.

13. The X-ray computed tomography apparatus according to claim 12, wherein the processor generates the second image by using, as the imaging plane, a figure having one selected from among rectangular, square, oval, and circular shapes to indicate the imaging position.

14. The X-ray computed tomography apparatus according to claim 13, wherein one of the shape and a size of the figure correspond to one of the following: one of a shape and a size of an opening formed in the gantry; and one of a shape and a size of a field of view with which the imaging process is performed by the gantry.

15. The X-ray computed tomography apparatus according to claim 12, wherein the processor generates the second image by combining together: one of a line and a plane corresponding to a median line of the subject, the first image, and the imaging plane.

16. The X-ray computed tomography apparatus according to claim 12, wherein the processor generates the plane related to the imaging plane corresponding to a tilting angle of the gantry.

17. The X-ray computed tomography apparatus according to claim 9, further comprising: an input interface circuit configured to change, in the second image displayed by a display circuit, one or both of the position and the angle of the imaging plane, in response to an input from a user, wherein
   on a basis of the imaging plane that has been changed, the processor controls at least one of: the gantry; and the couch.

18. The X-ray computed tomography apparatus according to claim 17, being provided with a portable terminal including the display circuit and the input interface circuit.

19. The X-ray computed tomography apparatus according to claim 12, wherein the first image renders one of the gantry and a reference position of the gantry.

20. A medical image diagnosis assisting method for assisting an image diagnosis process using a gantry that includes an imaging system configured to perform an imaging process on a subject by using one of radiation and magnetism, the medical image diagnosis assisting method comprising:
- generating a first image acquired by imaging the gantry and a couchtop of a couch on which the subject is placed while using an optical imaging device different from the imaging system;
- calculating, on a basis of a relative positional relationship between the gantry and the couchtop in the first image, at least one of position or angle of an imaging plane in the first image, the imaging plane being a plane related to an imaging position used in the imaging process by the imaging system;
- generating a second image by combining the first image with the imaging plane on a basis of the calculated at least one of position or angle; and
- displaying the second image.

* * * * *